US011045343B2

(12) United States Patent
Ostergard

(10) Patent No.: US 11,045,343 B2
(45) Date of Patent: Jun. 29, 2021

(54) HINGED ANKLE BRACE

(71) Applicant: Doak Ostergard, Lincoln, NE (US)

(72) Inventor: Doak Ostergard, Lincoln, NE (US)

( * ) Notice: Subject to any disclaimer, the term of this patent is extended or adjusted under 35 U.S.C. 154(b) by 1131 days.

(21) Appl. No.: 15/367,929

(22) Filed: Dec. 2, 2016

(65) Prior Publication Data

US 2018/0153724 A1 Jun. 7, 2018

(51) Int. Cl.
*A61F 5/00* (2006.01)
*A61F 5/01* (2006.01)

(52) U.S. Cl.
CPC .... *A61F 5/0127* (2013.01); *A61F 2005/0148* (2013.01); *A61F 2005/0165* (2013.01); *A61F 2005/0179* (2013.01)

(58) Field of Classification Search
CPC ...... A61F 2005/0148; A61F 2005/0179; A61F 2005/0165; A61F 2005/0169; A61F 2005/0197; A61F 5/0111; A61F 5/0113; A61F 5/0106; Y10T 403/455; Y10T 403/454; Y10T 403/32541; Y10T 403/32549; Y10T 403/32557; Y10T 403/45; Y10T 403/458; A63B 21/4025; A63B 21/4013; A63B 21/04–0407; A63B 21/0421; A63B 21/045
USPC ............................................ 403/22; 602/16
See application file for complete search history.

(56) References Cited

U.S. PATENT DOCUMENTS

| | | | | |
|---|---|---|---|---|
| 4,934,355 A * | 6/1990 | Porcelli | ................. | A61F 5/0127 602/16 |
| 5,069,202 A * | 12/1991 | Prock | .................... | A61F 5/0127 602/27 |
| 5,209,716 A * | 5/1993 | Frydman | .............. | A63B 21/028 482/121 |
| 5,263,911 A * | 11/1993 | Frydman | ............ | A63B 21/4025 482/124 |
| 7,753,866 B2 * | 7/2010 | Jackovitch | ............ | A61F 5/0127 602/27 |
| 8,641,654 B2 | 2/2014 | Verkade et al. | | |
| 9,364,366 B2 | 6/2016 | Verkade et al. | | |
| 10,226,373 B1 * | 3/2019 | McCoy | ................. | A61F 5/0125 |
| 2006/0084899 A1 | 4/2006 | Verkade et al. | | |
| 2011/0226385 A1 * | 9/2011 | Mitchell | ................. | B27B 31/04 144/335 |
| 2013/0075966 A1 * | 3/2013 | Carvey | ..................... | F16F 1/10 267/156 |
| 2014/0066829 A1 * | 3/2014 | Drillio | .................. | A61F 5/0127 602/27 |
| 2015/0216703 A1 * | 8/2015 | Madden | ................ | A61F 5/0127 602/7 |

FOREIGN PATENT DOCUMENTS

WO  WO-2010070364 A1 *  6/2010 ............ A61F 5/0113
WO  WQ-2010070364 A1 *  6/2010 ........... A61F 5/0127

* cited by examiner

*Primary Examiner* — Victoria J Hicks
*Assistant Examiner* — Kevin S Albers
(74) *Attorney, Agent, or Firm* — Dennis L. Thomte; Thomte Patent Law Office LLC

(57) ABSTRACT

A hinged ankle brace including a foot pad member and an ankle cuff which are hingedly secured together by flexible joint members. The flexible joint members yieldably resist hinged movement between the foot pad member and the ankle cuff.

2 Claims, 7 Drawing Sheets

HINGED ANKLE BRACE

BACKGROUND OF THE INVENTION

Field of the Invention

This invention relates to a hinged ankle brace and more particularly to a hinged ankle brace wherein the medial and lateral joints between the rigid foot bed member and the ankle cuff are floating flexible joints comprised of polyurethane or like materials. Even more particularly, the flexible joints create greater resistance to hinged movement of the foot bed member and the ankle cuff thereof as the two members hingedly move to a greater degree with respect to one another.

Description of the Related Art

Conventional semi-rigid ankle braces have been previously provided wherein the foot bed member of the ankle brace is pivotally or hingedly movable, about a pair of joints, with respect to the ankle cuff of the brace or vice versa. Normally, each of the prior art joints between the foot bed member and the ankle cuff are simply a pivotal pin or bolt. In such braces, the pivotal movement between the foot bed member and the ankle cuff is not a floating movement but is a pivotal movement about a central axis. Further, to the best of Applicant's knowledge, no one has provided a joint for hinged ankle braces which increases the resistance to pivotal movement as the pivotal movement between the foot bed member and the ankle cuff increases. In other words, in the prior art, any resistance to the pivotal movement between the foot bed member and the ankle cuff, if any, remains the same during the entire pivotal movement therebetween.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

The hinged ankle brace of this invention includes a foot bed member including a foot plate configured to underlie at least a portion of the foot of a wearer and a portion configured to receive a heel of the wearer. For purposes of description, the foot bed member will be described as having a medial side and a lateral side. A medial wing extends upwardly from the medial side of the foot bed member with the medial wing having a semi-circular upper end with inner and outer sides. A lateral wing extends upwardly from the lateral side of the foot bed member and has a generally semi-circular upper end with inner and outer sides. The ankle brace also includes an ankle cuff, having upper and lower ends, including a calf-supported portion configured to extend at least partially around the posterior side of the lower calf of a wearer. The ankle cuff has a medial side and a lateral side. The ankle cuff has a medial wing extending downwardly from the medial side thereof. The medial wing of the ankle cuff has a generally semi-circular lower end with inner and outer sides. The ankle cuff also has a lateral wing extending downwardly from the lateral side thereof. The lateral wing of the ankle cuff has a generally semi-circular lower end with inner and outer sides. The inner side of the lower end of the medial wing of the ankle cuff is positioned outwardly of the outer side of the upper end of the medial wing of the foot bed member. The inner side of the lower end of the lateral wing of the ankle cuff is positioned outwardly of the outer side of the upper end of the lateral wing of the foot bed member. The general shape of the foot bed member and the ankle cuff may vary.

A flexible medial joint member is positioned between the lower end of the medial wing of the ankle cuff and the upper end of the medial wing of the foot bed member. The flexible medial joint member hingedly connects the lower end of the medial wing of the ankle cuff to the upper end of the medial wing of the foot bed member.

A flexible lateral joint member is positioned between the lower end of the lateral wing of the ankle cuff and the upper end of the lateral wing of the foot bed member. The flexible lateral joint member hingedly connects the lower end of the lateral wing of the ankle cuff to the upper end of the lateral wing of the foot bed member.

The flexible joints create greater resistance to hinged movement of the foot bed member and the ankle cuff thereof as the two members hingedly move to a greater degree with respect to one another.

At least one strap is attached to the ankle cuff which is configured to secure a wearer's lower calf thereto. At least one strap may be attached to the foot bed member which is configured to secure a wearer's food thereto.

It is therefore a principal object of the invention to provide an improved hinged ankle brace.

A further object of the invention is to provide a hinged ankle brace wherein the foot pad member of the ankle brace is hingedly connected to the ankle cuff portion of the ankle brace wherein the joint members between the foot pad members and the ankle cuff are comprised of a flexible material wherein the resistance to the hinged movement between the foot pad member and the ankle cuff increasingly resists the hinged movement of the two members as the hinged movement of the two members increases.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DESCRIPTION OF THE PREFERRED EMBODIMENT

Figure 1:
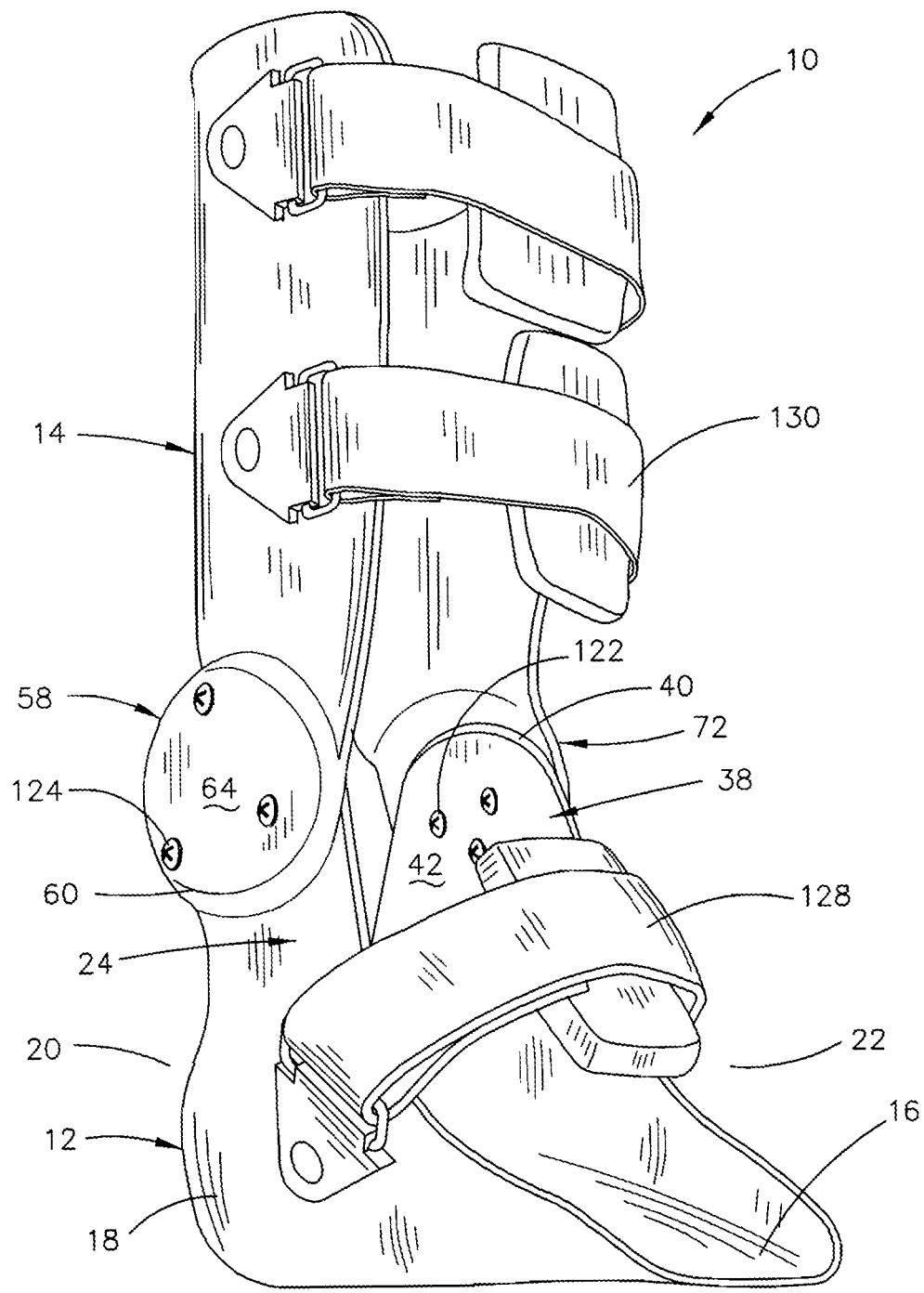
FIG. 1 is a perspective view of the hinged ankle brace of this invention.
Figure 2:
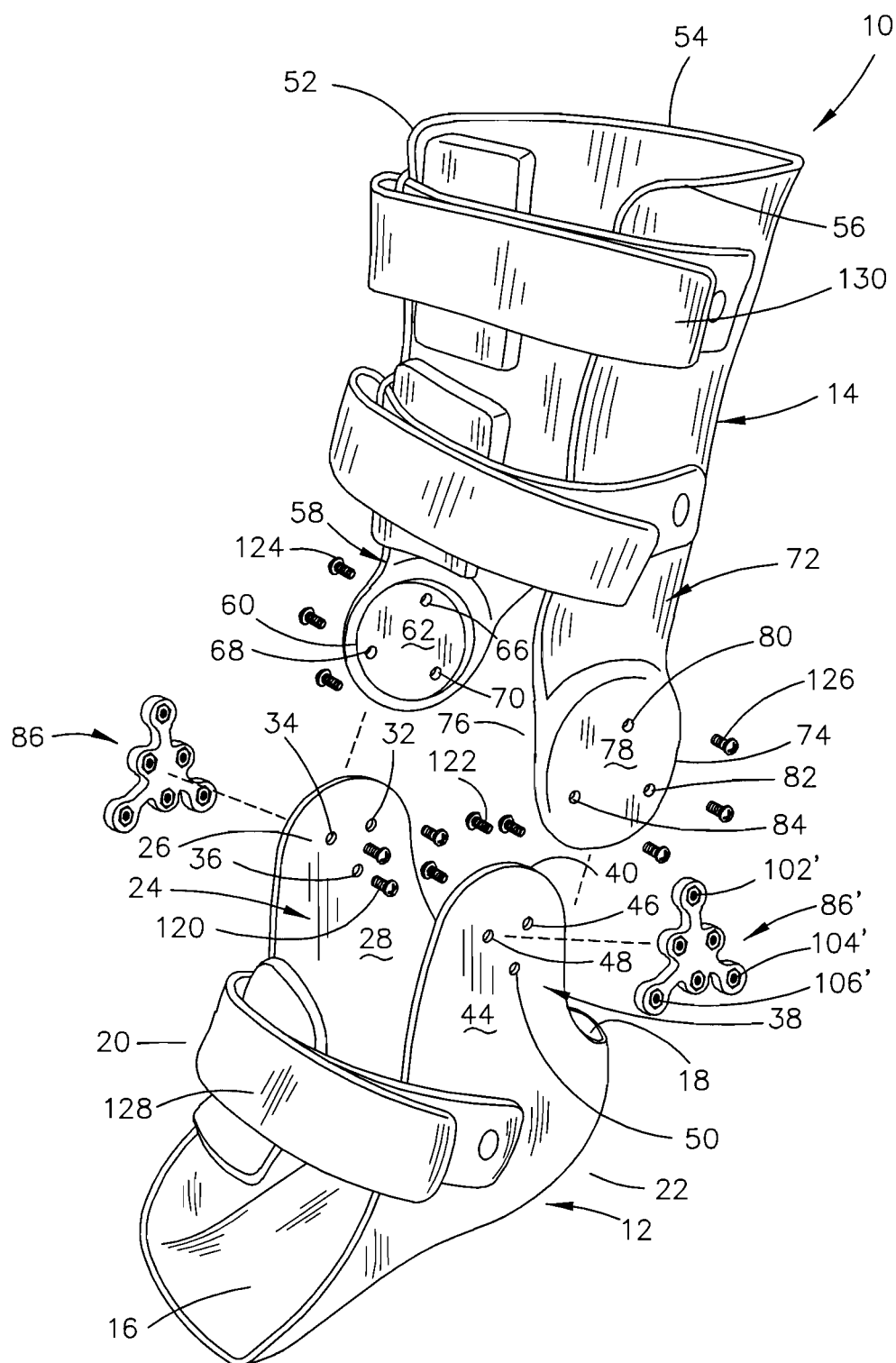
FIG. 2 is an exploded perspective view of the hinged ankle brace of this invention.
Figure 3:
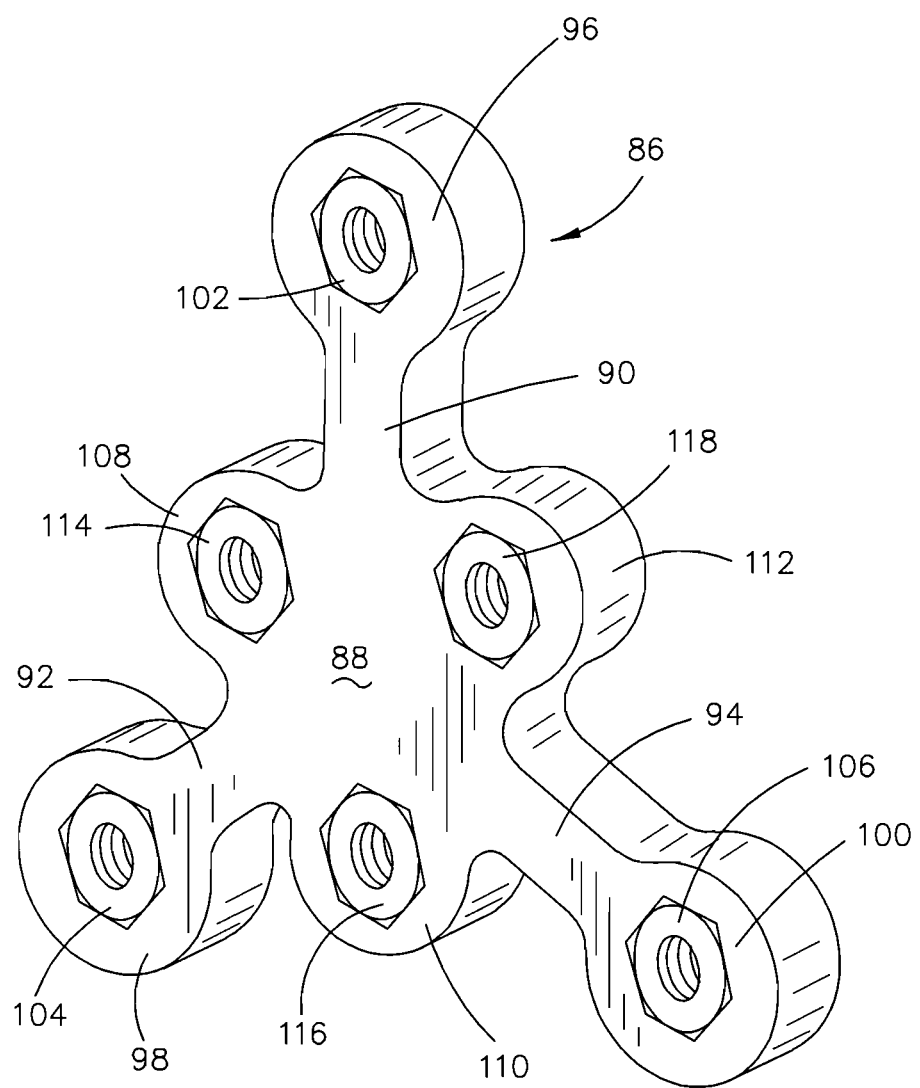
FIG. 3 is a perspective view of the flexible joint of the medial and lateral joints of the hinged ankle brace of this invention.
Figure 4:
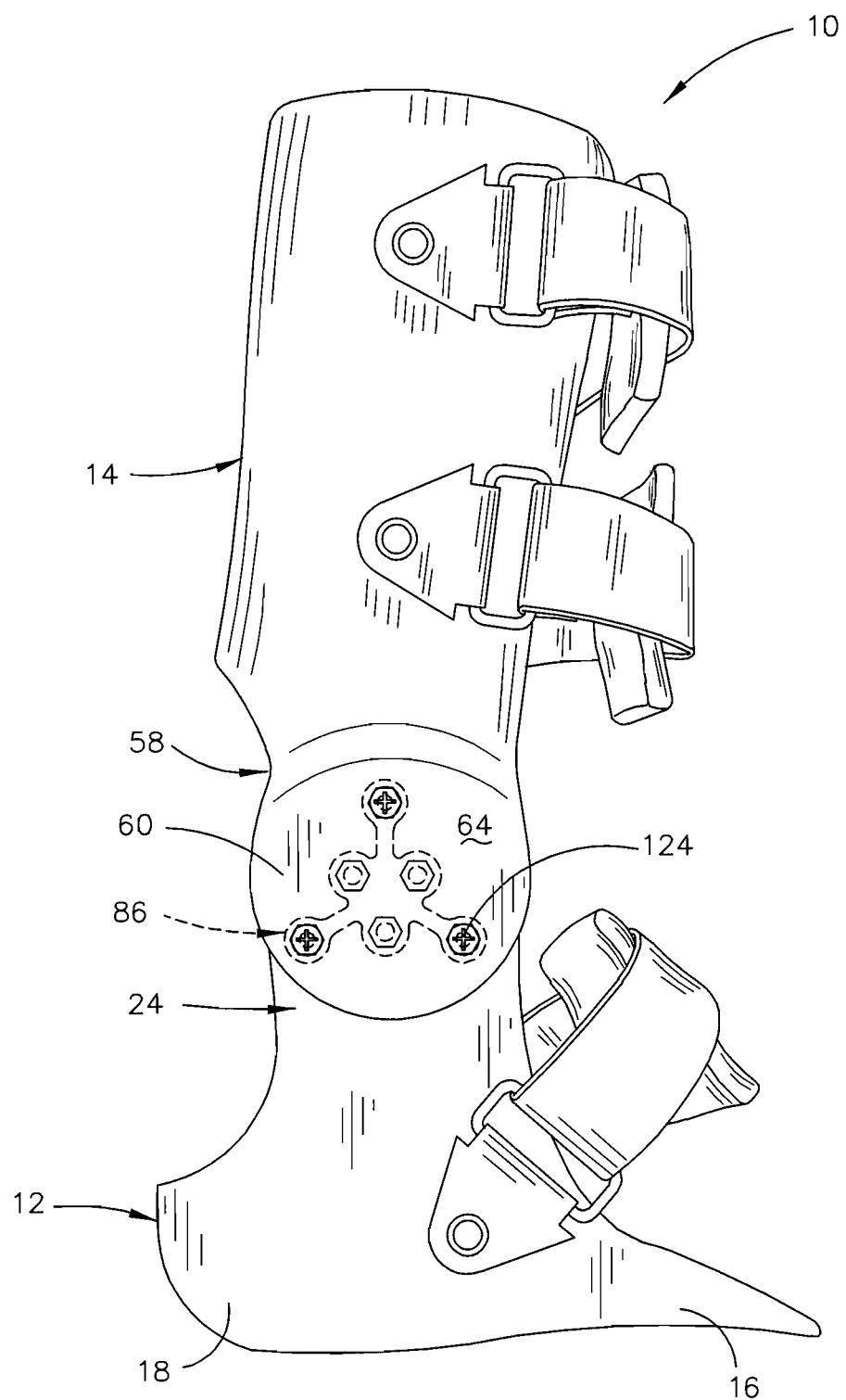
FIG. 4 is a medial side elevational view of the hinged ankle brace of this invention.
Figure 5:
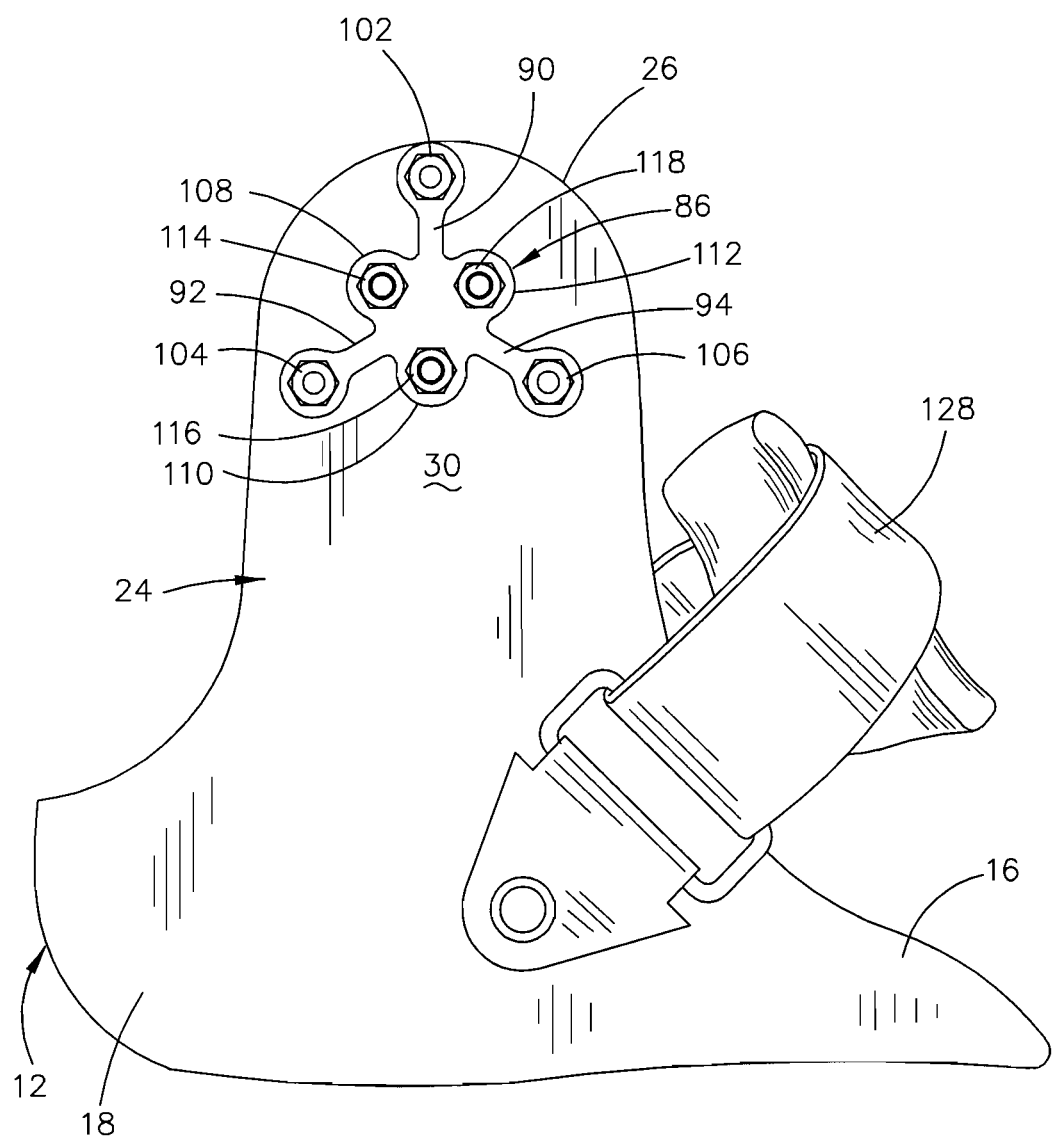
FIG. 5 is a medial side view of the foot bed member of the hinged ankle brace of this invention.

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The hinged ankle brace of this invention is designated by the reference numeral 10. Ankle brace 10 generally includes a foot pad member 12 and an ankle cuff 14 which are hingedly connected as will be described in detail hereinafter. The general shape of the foot pad member and the ankle cuff may vary. Ankle brace 10 will be described as being configured to be used with the left ankle and leg of a wearer. It should be understood that the ankle brace 10 could also be used to protect the right ankle of the wearer. The terms medial and lateral will apply to the left ankle brace with those terms being reversed for a right ankle brace. The brace 10 could also be easily designed to be a universal ankle brace suitable for use on either the right or left ankles.

Foot pad member 12 includes a foot plate 16 which is configured to underlie at least a portion of a foot of a wearer. Food pad member 12 also includes a heel portion 18 which is configured to receive a heel of the wearer. Foot pad member 12 will be described as having a medial side 20 and a lateral side 22. A medial wing 24 extends upwardly from the medial side 20 of the foot pad member 12. Medial wing 24 has a generally semi-circular upper end 26 with an inner side 28 and an outer side 30. Upper end 26 of medial wing 24 has three bolt openings 32, 34 and 36 formed therein. It should be noted that the upper end 26 of medial wing 24 could have more or less than three bolt openings formed therein.

A lateral wing 38 extends upwardly from the lateral side 22 of foot pad member 12. Lateral wing 38 has a generally semi-circular upper end 40 with an inner side 42 and an outer side 44. The upper end 40 of lateral wing 38 has three bolt openings 46, 48 and 50 formed therein. It should be noted that the upper end 40 of lateral wing 38 could have more or less than three bolt openings formed therein.

Ankle cuff 14 is designed to partially extend around the lower calf or leg of a person. Ankle cuff 14 includes a medial portion 52, a back portion 54 and a lateral portion 56. A medial wing 58 extends downwardly from the lower end of medial portion 52 and has a generally semi-circular lower end 60. Preferably, lower end 60 is slightly cup-shaped and has an inner side 62 and an outer side 64. Lower end 60 of medial wing 58 has radially spaced-apart bolt openings 66, 68 and 70 formed therein. Lower end 60 of medial wing 58 will have the same number of bolt openings as formed in upper end 26 of wing 24.

A lateral wing 72 extends downwardly from the lower end of lateral portion 56 of ankle cuff 14 and has a generally semi-circular lower end 74. Preferably, lower end 74 is slightly cup-shaped and has an inner side 76 and outer side 78. Lower end 74 of lateral wing 72 has radially spaced-apart bolt openings 80, 82 and 84 formed therein. Lower end 74 will have the same number of bolt openings as formed in the upper end 40 of wing 35.

The reference numeral 86 refers to a flexible medial joint member which hingedly connects medial wing 24 of foot pad portion 12 to medial wing 58 of ankle cuff 14. The numeral 86' refers to a flexible lateral joint member which is identical to joint member 86'. The designation "'" will be used to identify identical structure on joint member 86'.

Joint members 86 and 86' are comprised of a flexible polyurethane material or other similar material. Joint member 86 is flat and has an inner side and an outer side. Joint member 86 includes a center base portion 88 which has three support arms 90, 92 and 94 which extend outwardly from base portion 88 in a radially spaced-apart manner. Arms 90, 92 and 94 have enlarged head portions 96, 98 and 100 at their outer ends respectively. Nuts 102, 104 and 106 are embedded in head portions 96, 98 and 100 respectively.

Lobes or protrusions 108, 110 and 112 extend from base portion 88 in a radially spaced-apart manner. Nuts 114, 116 and 118 are embedded in lobes 108, 110 and 112 respectively.

Joint member 86 is positioned at the outer side 30 of upper end 26 of medial wing 24 of foot pad member 12 so that nuts 114, 116, and 118 thereof register with openings 34, 36 and 32 in the upper end 26 of wing 24. Bolts 120 are then extended outwardly through openings 32, 34 and 36 and threadably secured to nuts 114, 112 and 116 respectively to flexibly attach the joint member 86 to wing 24. Joint member 86' is positioned at the outer side of wing 38 and is attached to wing 38 by bolts 122 in a similar fashion to the manner in which joint member 86 is attached to wing 24 as explained above.

The ankle cuff 14 is then positioned relative to foot pad member 12 so that the wings 58 and 72 of ankle cuff 14 are positioned at the outer sides of joint members 86 and 86' respectively. Bolts 124 are then extended inwardly through bolt openings 66, 68 and 70 and into the nuts 102, 104 and 106 to flexibly attach the wing 58 to the wing 38. Bolts 126 are then extended inwardly through bolt openings 80, 82 and 84 and into the nuts 102', 104' and 106' of joint member 86' to flexibly attach wing 72 to wing 40. Although bolts 120, 122, 124 and 126 are shown and described, the bolts could be replaced with screws or rivets.

Figure 6B:
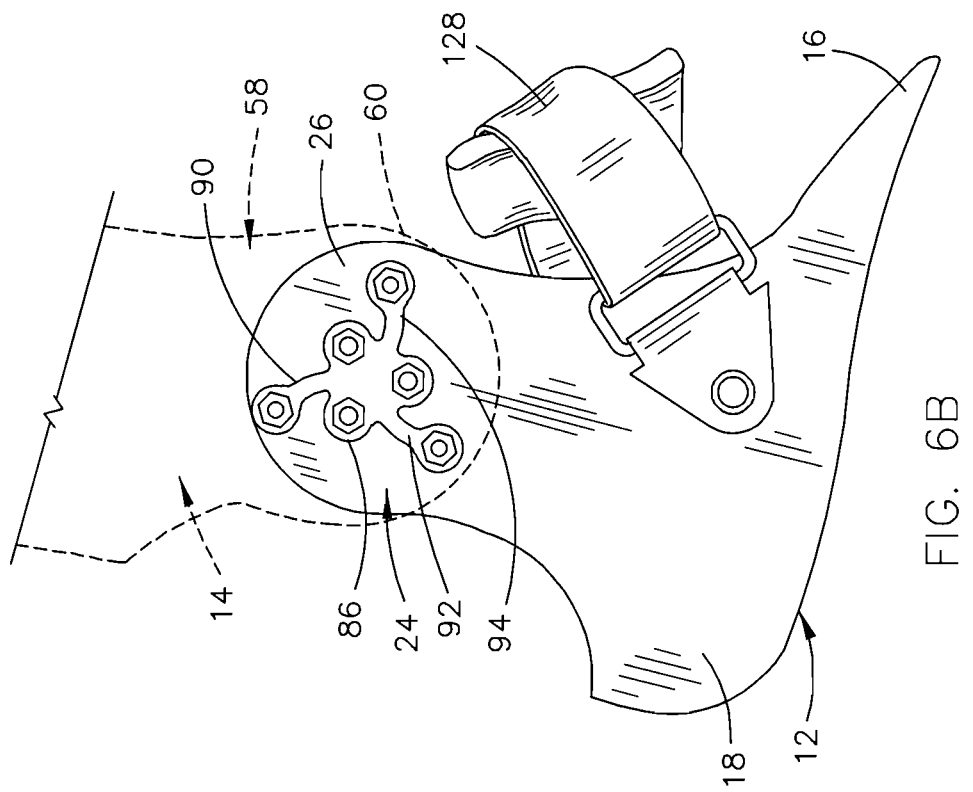
FIG. 6B is a medial side view of the foot bed member of the invention with the broken lines illustrating the lower medial side of the ankle cuff and which illustrates the manner in which the flexible medial joint yieldably resists the hinged movement of the ankle cuff with respect to the foot bed member.
Figure 6A:
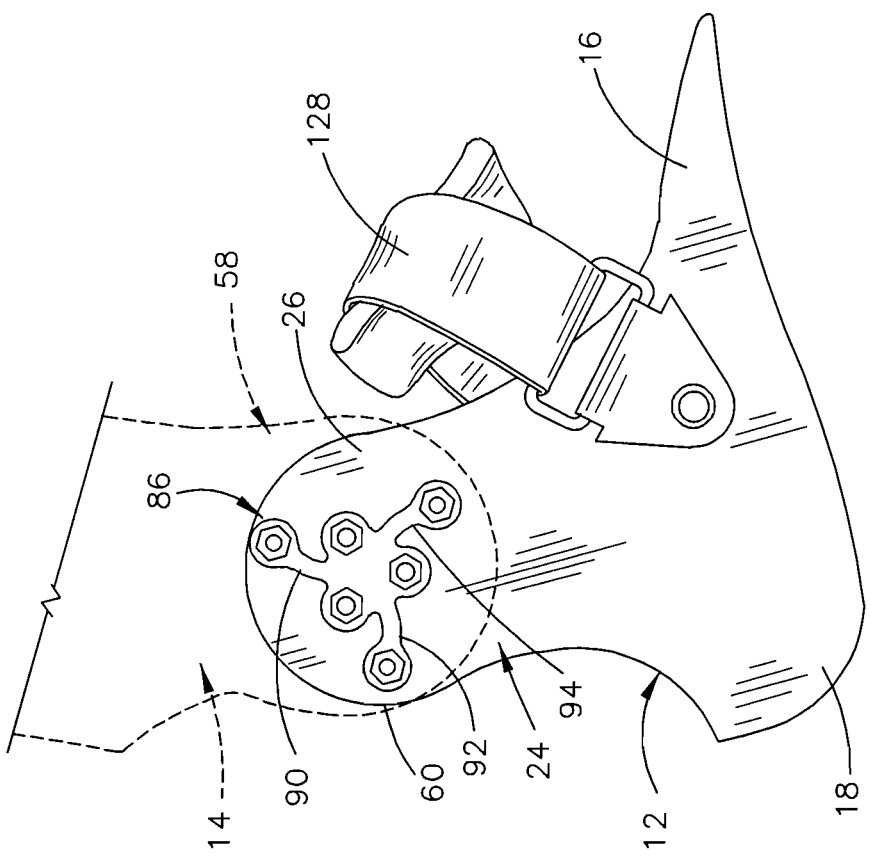
FIG. 6A is a medial side view of the foot bed member with the broken lines illustrating the lower medial side of the ankle cuff and which illustrates the manner in which the flexible medial joint yieldably resists the hinged movement of the foot bed member with respect to the ankle cuff.
Figure 7:
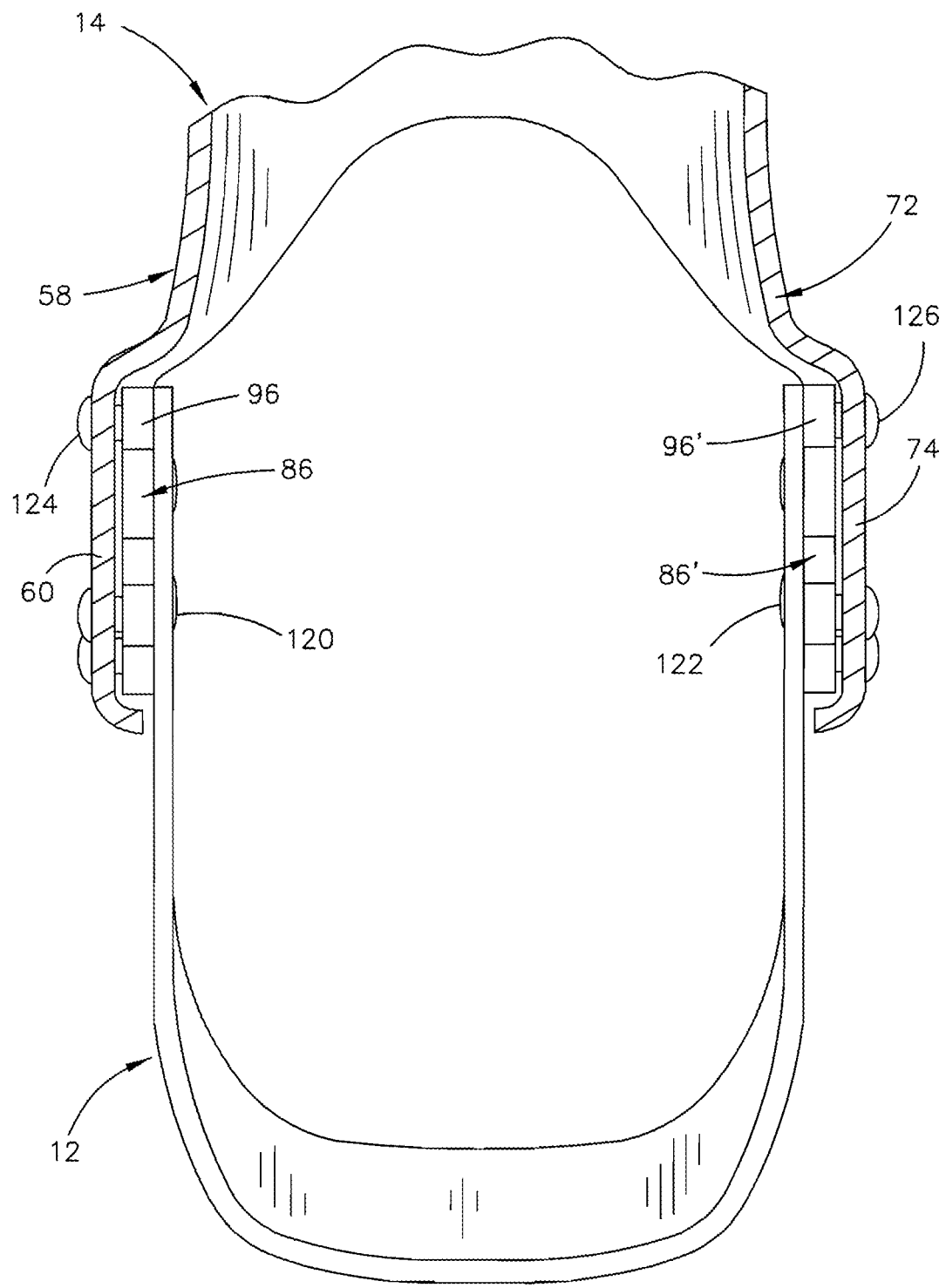
FIG. 7 is a partial vertical sectional view which illustrates the wings of the ankle cuff being secured to the wings of the foot bed member by way of the flexible medial joint and the flexible lateral joint.

The flexible joint members 86 and 86' yieldably resist relative hinged movement between the ankle cuff 14 and the foot pad member 12 as seen in FIGS. 6A and 6B. The joint members 86 and 86' provide a floating hinge connection between ankle cuff 14 and foot pad member 12. The flexible joint members 86 and 86' increase the resistance of movement between ankle cuff 14 and foot pad member 12 as the hinged movement therebetween increases. As seen in FIGS. 6A and 6B, the arms of the joint member 86 bend during hinged movement of ankle cuff 14 relative to foot pad member 12. As the arms of joint member 86 bend, they create more resistance to the hinged movement.

The hinged ankle brace 10 of this invention includes at least one strap 128 affixed thereto to maintain the wearer's foot in foot pad member 12. In some cases, it may not be necessary to utilize the strap 128. The hinged ankle brace 10 also includes at least one strap 130 affixed thereto to attach the ankle cuff 14 to the wearer's lower leg.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

I claim:

1. A hinged ankle brace, comprising:
   a foot bed member including a foot plate configured to underlie at least a portion of a foot of a wearer and a portion configured to receive a heel of the wearer;
   said foot bed member having a medial side and a lateral side;
   a medial wing extending upwardly from said medial side of said foot bed member;
   said medial wing of said foot bed member having an upper end with inner and outer sides;
   a lateral wing extending upwardly from said lateral side of said foot bed member;
   said lateral wing of said foot bed member having an upper end with inner and outer sides;
   an ankle cuff, having upper and lower ends, including a calf-supporting portion configured to extend at least partially around a posterior side of a lower calf of a wearer;
   said ankle cuff having a medial side and a lateral side;
   said ankle cuff having a medial wing extending downwardly from said medial side of said ankle cuff;
   said medial wing of said ankle cuff having a lower end with inner and outer sides;
   said ankle cuff having a lateral wing extending downwardly from said lateral side of said ankle cuff;
   said lateral wing of said ankle cuff having a lower end with inner and outer sides;
   said inner side of said lower end of said medial wing of said ankle cuff being positioned outwardly of said outer side of said upper end of said medial wing of said foot bed member;
   said inner side of said lower end of said lateral wing of said ankle cuff being positioned outwardly of said outer side of said upper end of said lateral wing of said foot bed member;
   a flat flexible medial joint member positioned between said lower end of said medial wing of said ankle cuff and said upper end of said medial wing of said foot bed member;
   said flat flexible medial joint member hingedly connecting said lower end of said medial wing of said ankle cuff to said upper end of said medial wing of said foot bed member;
   a flat flexible lateral joint member positioned between said lower end of said lateral wing of said ankle cuff and said upper end of said lateral wing of said foot bed member;
   said flat flexible lateral joint member hingedly connecting said lower end of said lateral wing of said ankle cuff to said upper end of said lateral wing of said foot bed member;
   said flat flexible medial joint member including:
   (a) a flat base portion having an inner side and an outer side;
   (b) said flat base portion having a plurality of radially spaced-apart nut receiving portions formed therein;
   (c) each of said radially spaced-apart nut receiving portions of said flat base portion having an internally threaded nut embedded therein;
   (d) said flat base portion having a plurality of radially spaced-apart arms extending therefrom with each of said arms having inner and outer ends;
   (e) each of said arms having nut receiving portions at said outer end thereof;
   (f) each of said nut receiving portions of said arms having an internally threaded nut embedded therein;
   a plurality of threaded first bolts, having outer and inner ends, extending inwardly through said lower end of said medial wing of said ankle cuff in a radially spaced-apart manner;
   said inner ends of said first bolts extending into said outer side of said base member and being threadably secured to said nuts in said nut receiving portions of said arms of said flat flexible medial joint member;
   a plurality of threaded second bolts, having outer and inner ends, extending inwardly through said upper end of said medial wing of said foot bed member in a radially spaced-apart member;
   said inner ends of said second bolts extending into said inner side of said base member and being threadably secured to said nuts in said nut receiving portions in said base portion of said flat flexible medial joint member;
   said flat flexible lateral joint member including:
   (a) a flat base portion having an inner side and an outer side;
   (b) said flat base portion having a plurality of radially spaced-apart nut receiving portions formed therein;
   (c) each of said radially spaced-apart nut receiving portions having an internally threaded nut embedded therein;
   (d) said flat base portion having a plurality of radially spaced-apart arms extending therefrom with each of said arms having inner and outer ends;
   (e) each of said arms having nut receiving portions at said outer end thereof;
   (f) each of said nut receiving portions of said arms having an internally threaded nut embedded therein;
   a plurality of threaded third bolts, having outer and inner ends, extending inwardly through said lower end of said lateral wing of said ankle cuff in a radially spaced-apart manner;
   said inner ends of said third bolts extending into said outer side of said base member of said lateral joint member and being threadably secured to said nuts in said nut receiving portions of said arms of said flat flexible lateral joint member;
   a plurality of threaded fourth bolts, having outer and inner ends, extending outwardly through said upper end of said lateral wing of said foot bed member in a radially spaced-apart member;
   said inner ends of said fourth bolts extending into said inner side of said base member of said lateral joint member and being threadably secured to said nuts in said nut receiving portions in said base portion of said flexible lateral joint member;
   said flexible medial and lateral joint members yieldably resisting the hinged movement between said foot pad member and said ankle cuff with said medial and lateral joint members increasingly yieldably resisting the hinged movement between said foot pad member and said ankle cuff as the hinged movement therebetween increases; and at least one strap attached to said ankle cuff configured to secure a wearers lower calf thereto.

2. The hinged ankle brace of claim 1 wherein a strap is attached to said foot bed member which is configured to secure a wearer's foot thereto.

\* \* \* \* \*